US011686426B2

(12) United States Patent
Hahn et al.

(10) Patent No.: US 11,686,426 B2
(45) Date of Patent: Jun. 27, 2023

(54) TRAY ARM ASSEMBLY INCLUDING A JOINT WITH A TWO-TIER FRICTION MECHANISM

(71) Applicant: Alcon Inc., Fribourg (CH)

(72) Inventors: Andrew Mason Hahn, Anaheim, CA (US); Marc Nestor, Aliso Viejo, CA (US); Scott Newton, Costa Mesa, CA (US); Paul Seiter, San Diego, CA (US)

(73) Assignee: Alcon Inc., Fribourg (CH)

( * ) Notice: Subject to any disclaimer, the term of this patent is extended or adjusted under 35 U.S.C. 154(b) by 158 days.

(21) Appl. No.: 16/942,868

(22) Filed: Jul. 30, 2020

(65) Prior Publication Data
US 2021/0041055 A1   Feb. 11, 2021

Related U.S. Application Data

(60) Provisional application No. 62/884,762, filed on Aug. 9, 2019.

(51) Int. Cl.
| *F16M 11/18* | (2006.01) |
| *F16M 11/20* | (2006.01) |
| *F16D 7/02* | (2006.01) |
| *F16D 13/60* | (2006.01) |
| *F16D 13/68* | (2006.01) |
| *F16C 11/10* | (2006.01) |

(52) U.S. Cl.
CPC ....... *F16M 11/2042* (2013.01); *F16C 11/103* (2013.01); *F16D 7/025* (2013.01); *F16D 13/60* (2013.01); *F16D 13/683* (2013.01); *F16M 11/18* (2013.01); *Y10T 403/32319* (2015.01)

(58) Field of Classification Search
CPC ... F16M 11/2042; F16M 11/18; F16C 11/103; F16D 7/025; F16D 13/60; F16D 13/683
USPC ......................................................... 52/36.1
See application file for complete search history.

(56) References Cited

U.S. PATENT DOCUMENTS

| 5,683,064 | A | | 11/1997 | Copeland et al. | |
|---|---|---|---|---|---|
| 5,779,209 | A | * | 7/1998 | Rello | F16M 11/10 248/278.1 |
| 6,719,113 | B2 | | 4/2004 | Bonser | |
| 6,736,360 | B1 | | 5/2004 | Buczek | |
| 7,461,825 | B2 | | 12/2008 | Olivera et al. | |
| 7,565,972 | B2 | | 7/2009 | Steppe | |

(Continued)

FOREIGN PATENT DOCUMENTS

| JP | 5358400 B2 | 12/2013 |
|---|---|---|
| WO | 2018229545 A1 | 12/2018 |
| WO | 2020144660 A1 | 7/2020 |

*Primary Examiner* — Mark R Wendell
(74) *Attorney, Agent, or Firm* — Patterson + Sheridan, L.L.P.

(57) ABSTRACT

Particular embodiments disclosed herein provide a joint of a tray arm assembly, comprising a joint body, a shaft configured to rotate relative to the joint body about a longitudinal axis of the shaft, and a slip clutch assembly, comprising a clutch stack, including a plurality of first clutch plates keyed to the shaft and a plurality of second clutch plates keyed to the joint body. The clutch stack further comprises a spring configured to selectively exert a force on the clutch stack, wherein the force compresses the clutch stack causing a friction between the plurality of first clutch plates and the plurality of second clutch plates with respect to a rotation of the shaft relative to the joint body.

15 Claims, 12 Drawing Sheets

(56) References Cited

U.S. PATENT DOCUMENTS

| | | |
|---|---|---|
| 7,886,671 B2 | 2/2011 | Roberge et al. |
| 8,310,468 B2 | 11/2012 | Martin |
| 8,474,771 B2 | 7/2013 | Ross |
| 8,684,145 B2 | 4/2014 | Boukhny |
| 9,581,190 B2 | 2/2017 | Richman |
| 9,615,930 B2 | 4/2017 | Katrana |
| 9,939,603 B2 | 4/2018 | Vasseur |
| 10,670,825 B2 | 6/2020 | Foes et al. |
| 10,851,938 B2 | 12/2020 | Glickstein et al. |
| 11,027,438 B2 | 6/2021 | Keen et al. |
| 11,530,774 B2 | 12/2022 | Borloz et al. |
| 2003/0117727 A1* | 6/2003 | Weber ................ G02B 21/24 359/431 |
| 2008/0067302 A1* | 3/2008 | Olivera ............... F16M 11/08 248/183.1 |
| 2015/0243267 A1* | 8/2015 | Miyajima .......... F16M 11/2014 84/421 |
| 2018/0014906 A1* | 1/2018 | Fukushima ....... G02B 21/0012 |
| 2020/0191322 A1 | 6/2020 | Honaryar |
| 2022/0047352 A1 | 2/2022 | Cuzner et al. |

* cited by examiner

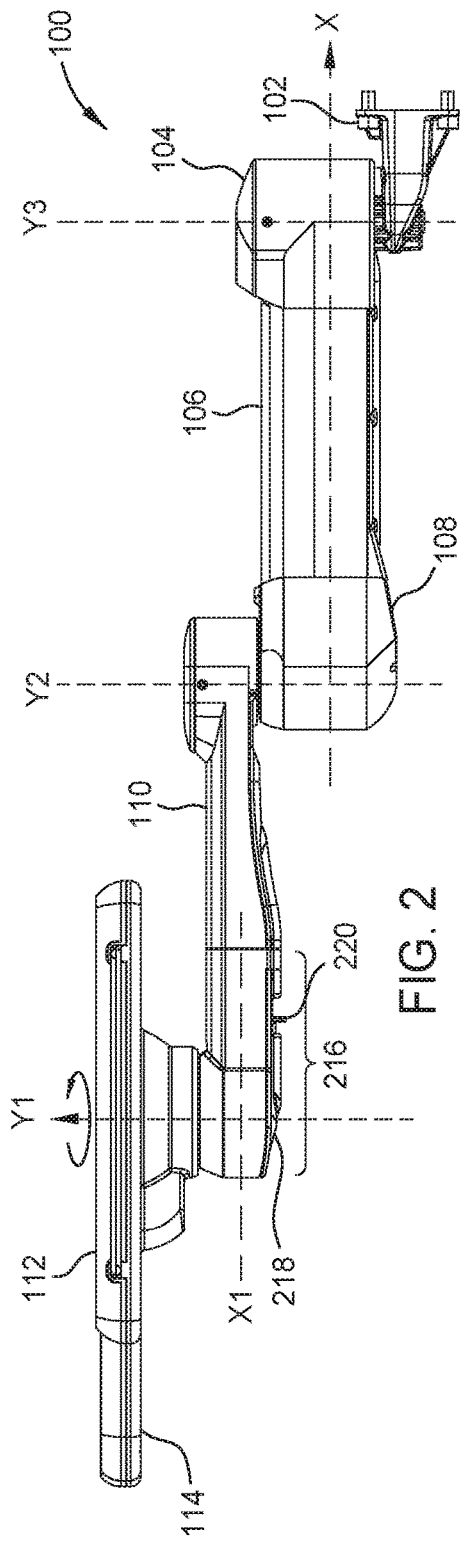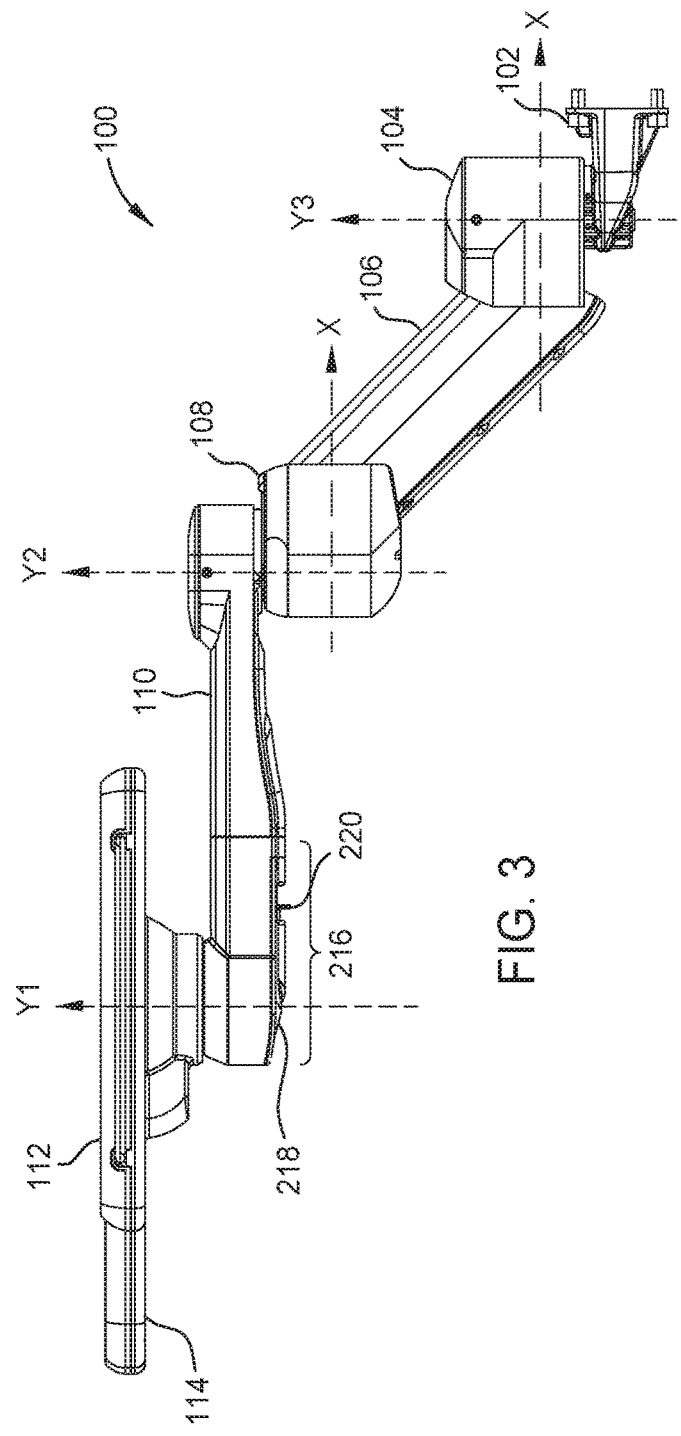

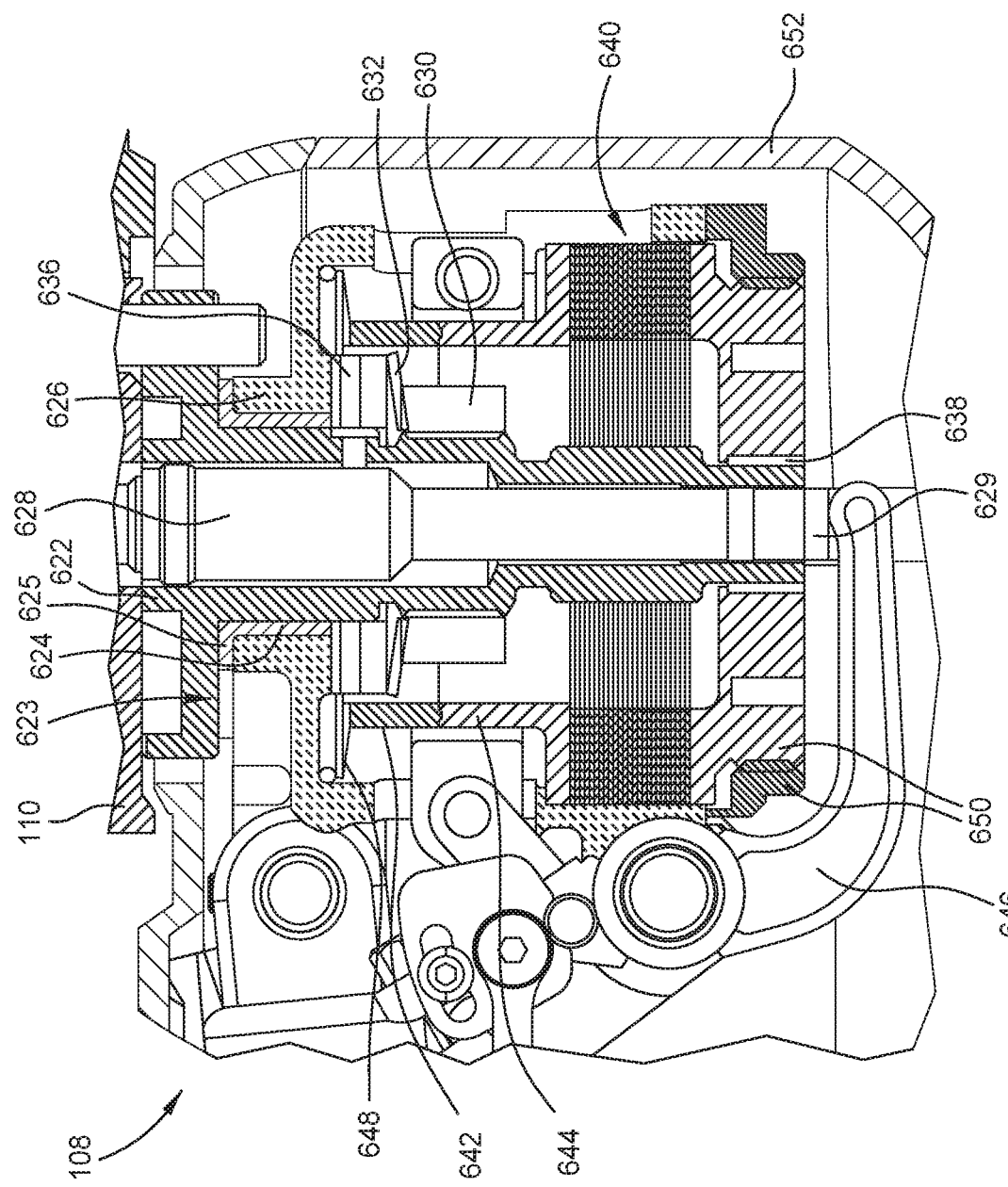

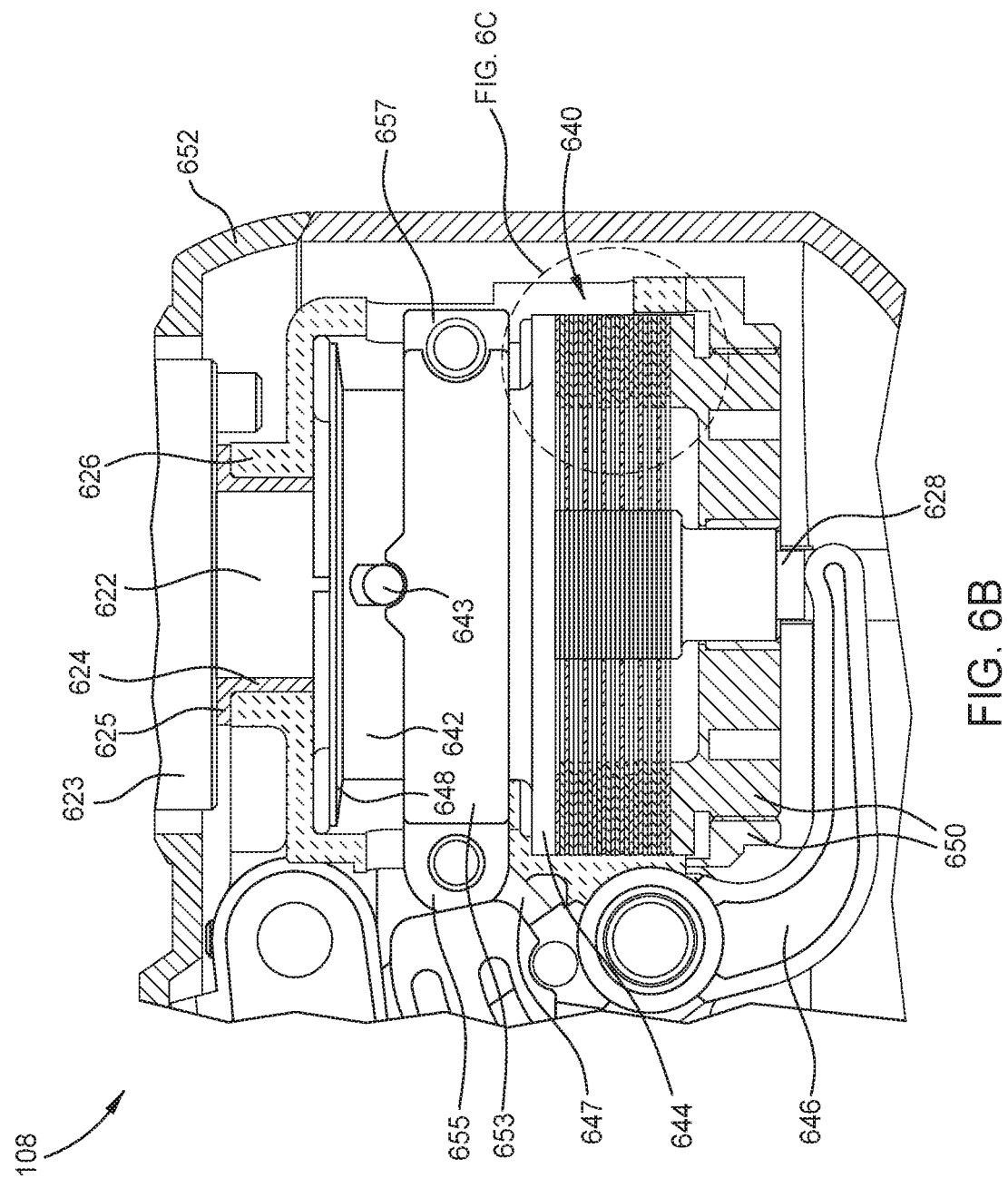

TRAY ARM ASSEMBLY INCLUDING A JOINT WITH A TWO-TIER FRICTION MECHANISM

PRIORITY CLAIM

This application claims the benefit of priority of U.S. Provisional Patent Application Ser. No. 62/884,762 titled "TRAY ARM ASSEMBLY INCLUDING A JOINT WITH A TWO-TIER FRICTION MECHANISM," filed on Aug. 9, 2019, whose inventors are Andrew Mason Hahn, Marc Nestor, Scott Newton and Paul Seiter, which is hereby incorporated by reference in its entirety as though fully and completely set forth herein.

TECHNICAL FIELD

The present disclosure relates generally to a tray arm assembly including a joint with a two-tier friction mechanism.

BACKGROUND

In many types of equipment, particularly medical equipment, a health care professional uses an array of instruments to perform delicate procedures, such as surgery, on a patient. These instruments together with certain supplies and consumables are typically placed on a tray located both near the patient and within easy reach of the health care professional. Most people who have ever visited a dentist are familiar with the tray used by a dental hygienist or a dentist when performing either cleaning or more complex dental procedures on teeth. The tray is positioned near the dental patient's mouth so that those items needed to complete a procedure are in easy reach of the health care professional.

Trays such as those used by dentists are also used with other types of equipment to conduct medical procedures such as those conducted in an operating room while a patient may be under anesthesia. One example of such procedures is eye surgery. A medical procedure such as eye surgery requires that the needed instruments, supplies and consumables be placed near the eyes of the patient but also that these instruments, supplies and consumables be within easy reach of the eye surgeon.

During certain types of eye surgery the surgeon typically is positioned over the head of the patient to enable easy access to the eyes of the patient. The surgeon then uses a variety of different instruments, supplies and consumables during the eye surgery procedure. These instruments, supplies and consumables may be placed within easy reach of the surgeon on a tray that may be coupled to a surgical console through a tray arm assembly.

Certain existing tray arm assemblies include one or more joints, which allow a user, such as a surgeon, to move the tray relative to the console. For example, a tray arm assembly may include an upper arm that couples to the console through a shoulder joint, a forearm that couples to the upper arm through an elbow joint, and a wrist joint that couples the forearm to the tray. Each of these joints allows the tray to move about the joint. Some of these existing tray arm assemblies are configured such that their respective joints can be locked to ensure that the tray does not move in response to an inadvertent contact with, for example, a user. However, in certain cases, a user may wish to move a tray relative to the console, which may cause the locked joints to break if the user applies excessive force on the tray arm assembly. Some of the other existing tray arm assemblies do not provide any mechanisms, such as a locking mechanism, to prevent the tray from moving in response to an inadvertent contact with a user. In such cases, as a result of the application of a small amount of force to the tray, the tray may move or rotate excessively.

BRIEF SUMMARY

The present disclosure relates generally to a tray arm assembly including a joint with a two-tier friction mechanism.

Particular embodiments disclosed herein provide a joint of a tray arm assembly, comprising a joint body, a shaft configured to rotate relative to the joint body about a longitudinal axis of the shaft, and a slip clutch assembly, comprising a clutch stack, including a plurality of first clutch plates keyed to the shaft and a plurality of second clutch plates keyed to the joint body. The clutch stack further comprises a spring configured to selectively exert a force on the clutch stack, wherein the force compresses the clutch stack causing a friction between the plurality of first clutch plates and the plurality of second clutch plates with respect to a rotation of the shaft relative to the joint body.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 2 illustrates a side view of the tray arm assembly of FIG. 1 in an un-elevated state, in accordance with certain embodiments of the present disclosure.

FIG. 3 illustrates a side view of the tray arm assembly of FIG. 1 in an elevated state, in accordance with certain embodiments of the present disclosure.

FIGS. 6A-6B illustrate an example two-tier friction mechanism of an elbow joint and its corresponding components, in accordance with certain embodiments of the present disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide a tray arm assembly including a joint with a two-tier friction mechanism. While the embodiments below describe a tray arm assembly used in connection with a surgical console, such as an ophthalmic surgical console, those of ordinary skill in the art appreciate that the disclosed tray arm assembly may be used with a variety of other consoles or equipment. For example, the tray arm assembly described herein may be used in conjunction with non-medical equipment.

Figure 1:
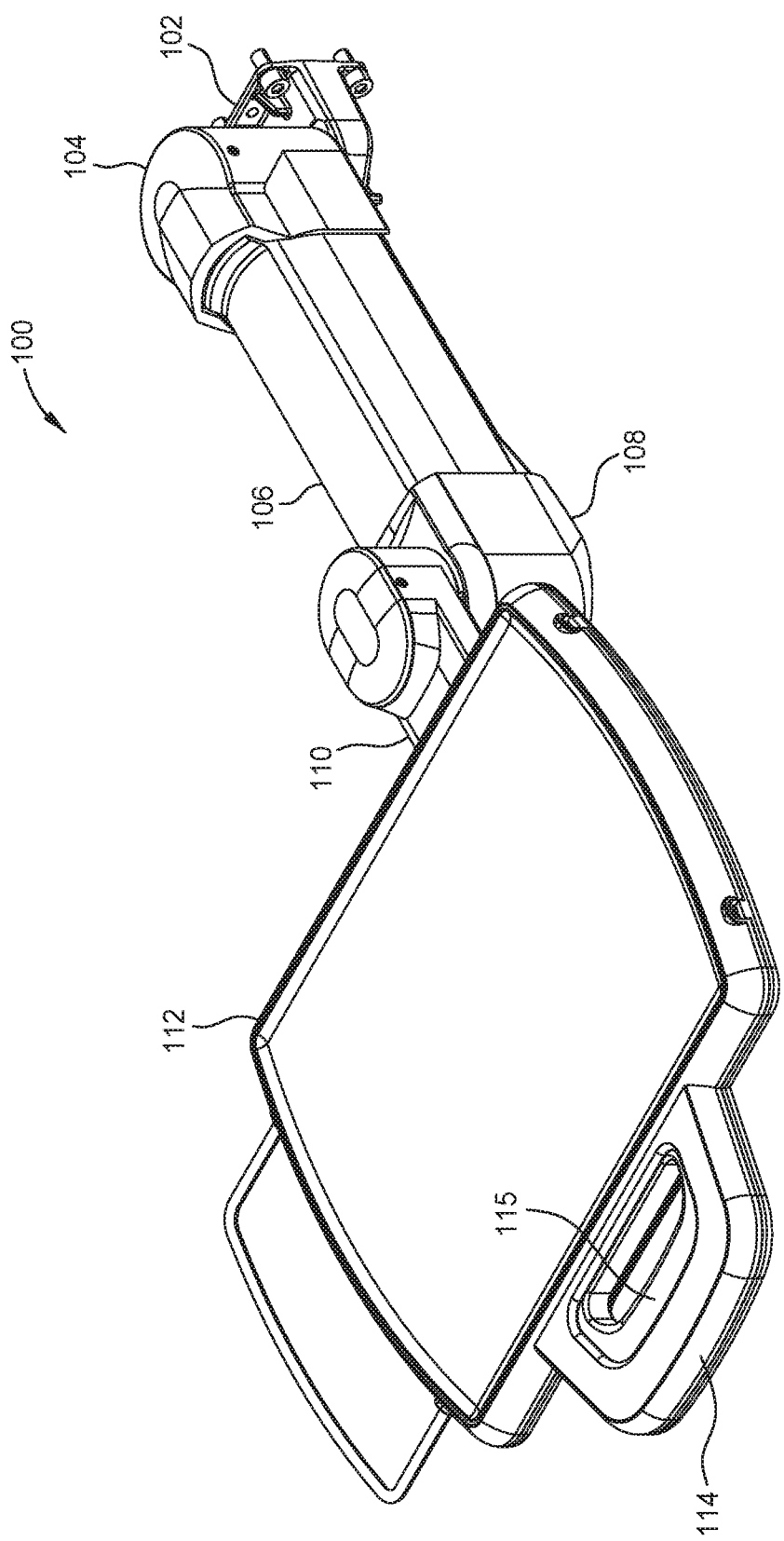
FIG. 1 illustrates a tray arm assembly, in accordance with certain embodiments of the present disclosure.

FIG. 1 illustrates a tray arm assembly 100, which is constructed to be an integral part of a surgical console. Tray arm assembly 100 may be mounted on the console using mount 102. As shown, tray arm assembly 100 comprises a shoulder joint 104, an upper arm assembly 106, an elbow joint 108, a forearm assembly 110, a tray joint, a tray 112, a tray positioning handle 114, and a release handle 115. Shoulder joint 104, elbow joint 108, and the tray joint may hereinafter be referred to as "the joints." Tray 112 provides a useful surface with the capacity to hold instruments, equipment and consumables as well as the ability to hold cable and tubes during a surgical procedure. Note that an example of a surgical console to which tray arm assembly 100 may be coupled is shown and described in U.S. Pat. No. 7,461,825, which was filed Dec. 9, 2008. The aforementioned application is herein incorporated by reference in its entirety.

Shoulder joint 104, elbow joint 108, and the tray joint are configured to allow tray 112 to be positioned (e.g., moved or rotated) with respect to the console, as described in further detail below. Also, one or more (e.g., each) of shoulder joint 104, elbow joint 108, and the tray joint comprises a two-tier friction mechanism. The two-tier friction mechanism within each joint, as described in further detail in relation to FIGS. 6A/6B, comprises a first friction mechanism and a second friction mechanism. If activated, the first friction mechanism prevents any movement in the joint unless enough torque is applied to the joint to overcome the friction associated with the first friction mechanism. In other words, when the first friction mechanism is activated in all the joints, a user is not able to move or rotate tray arm assembly 100 relative to the console unless the user applies enough torque to overcome the first friction mechanism in one or more of the joints. Once enough torque is applied to a joint and the first friction mechanism is overcome, the corresponding components that are coupled to the joint can be moved or rotated relative to the console.

By grabbing and pulling release handle 115, a user is able to deactivate the first friction mechanism in every joint with a first friction mechanism in order to position tray 112 with respect to the console. However, even with the first friction mechanism de-activated, each joint is still subject to a second friction mechanism, which is always active in the joint. The second friction mechanism subjects each joint to a drag torque, which prevents the whipping of tray arm assembly 100 relative to the console. Drag torque is exerted in each joint by the second friction mechanism in the opposite direction of torque applied to the joint. Note that applying torque to a joint herein may include applying torque to one or more of the components that are coupled to the joint. For example, applying torque to elbow joint 108 includes or can be caused by applying torque to forearm assembly 110 and upper arm 106. In another example, applying torque to shoulder joint 104 includes applying torque to forearm assembly 110 and the console.

By releasing the release handle 115, a user is able to re-activate the first friction mechanism in the joints. When the first friction mechanism is activated, an application of force to one or more components of tray arm assembly 100 does not cause any movement or rotation in tray arm assembly 100 relative to the console, unless such a force results in torque exceeding a threshold amount of torque required to overcome the first friction mechanism in one or more of the joints. As such, when the first friction mechanism is activated in the joints, a user is able to grab tray positioning handle 114 and move the console by pushing and pulling handle 114 or any other part of tray 112, upper arm assembly 106, forearm assembly 110, etc.

The first friction mechanism also ensures that tray arm assembly 100's joints are not damaged as a result of excessive torque applied thereto. This is because, in response to excessive torque, the first friction mechanism is overcome in a joint, allowing for movement or rotation. This is unlike certain prior art tray arm assemblies whose components are not configured to move regardless of how much force is applied thereto. With such prior art tray arm assemblies, a user may apply excessive torque on one or more of the joints, with the intention of, for example, rotating the tray relative to console, which may cause damage to such joints.

The two-tier friction mechanism is described in relation to FIGS. 6A-11 with more detail. Note that the tray arm assembly 100 described herein is entirely mechanical, however, those of ordinary skill in the art will understand that in an alternate embodiment one or more powered actuators may be used to move the components, including the arm assemblies and joints of tray arm assembly 100.

FIG. 2 illustrates a side view of tray arm assembly 100 in an un-elevated state. As shown, tray arm assembly 100 further comprises a tray joint 218, which allows tray 112 to rotate in relation to forearm assembly 110. More specifically, tray joint 218 allows tray 112 to rotate around a $Y_1$ axis of tray joint 218, where the $Y_1$ axis is perpendicular to a longitudinal axis (i.e., the $X_1$ axis) of the forearm assembly 110. Similarly, elbow joint 108 allows forearm assembly 110 to rotate around a $Y_2$ axis of elbow joint 108. Also, shoulder joint 104 allows upper arm 106 to rotate around a $Y_3$ axis of shoulder joint 104. Tray arm assembly 100 also comprises a storage control handle 220 that actuates a wrist rotation mechanism. By pulling storage control handle 220 a user is able to rotate a wrist 216, which is a portion of forearm assembly 110, around the longitudinal axis of forearm assembly 110 (i.e., the $X_1$ axis), as further shown in FIG. 5.

FIG. 3 illustrates tray arm assembly 100 in an elevated state. As shown, shoulder joint 104, elbow joint 108, and upper arm 106 are configured as links in a 4-bar mechanism. A user is able to elevate tray arm assembly 100 by pulling release handle 115, which not only de-activates the first friction mechanism in each of the joints but it also unlocks the elevation adjustment mechanism in upper arm 106. The 4-bar mechanism allows the forearm and tray to maintain a horizontal orientation relative to the ground regardless of the tray's elevation.

Figure 4:
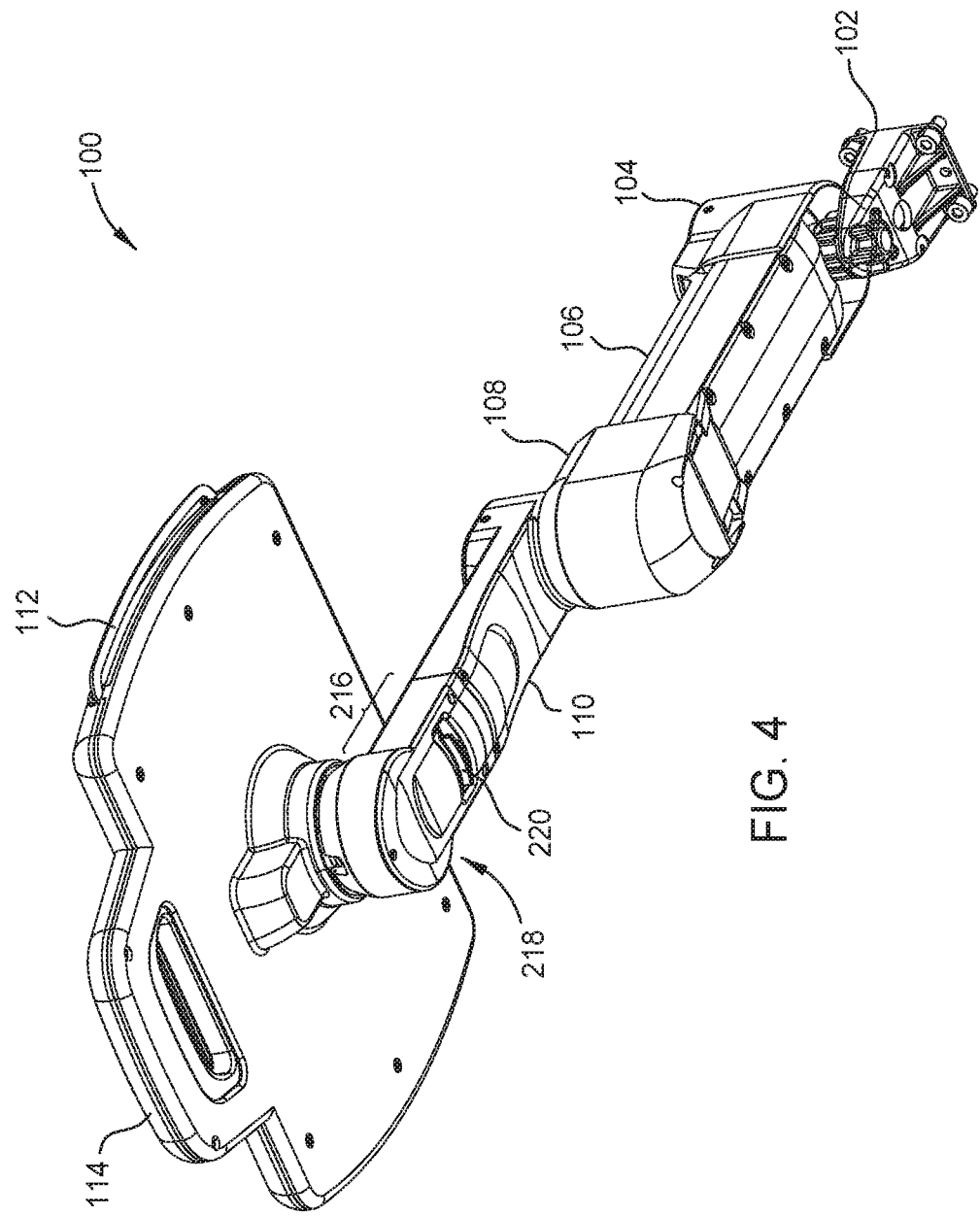
FIGS. 4 and 5 illustrate a wrist rotation mechanism of the tray arm assembly of FIG. 1, in accordance with certain embodiments of the present disclosure.
Figure 5:
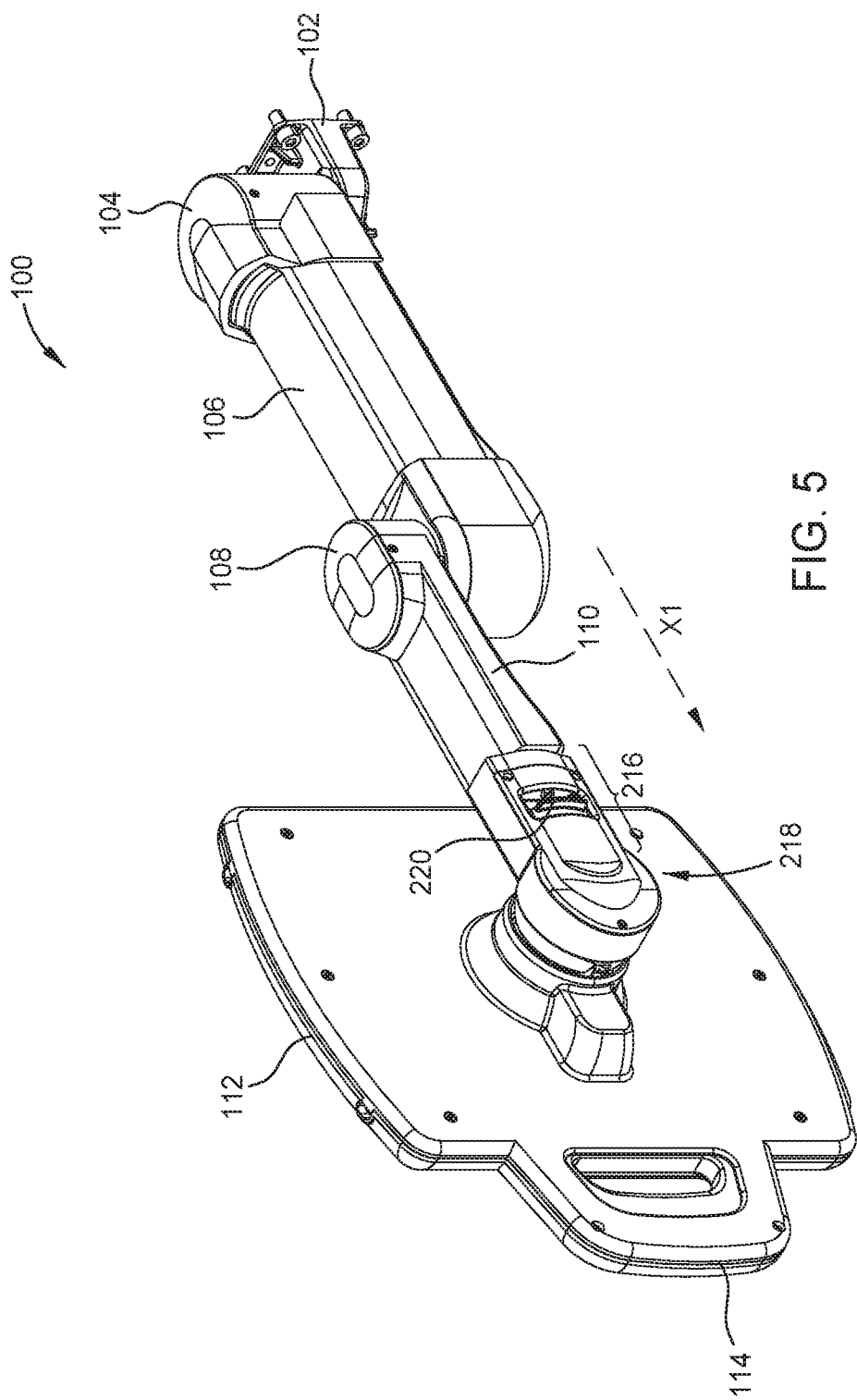

FIGS. 4 and 5 illustrate the wrist rotation mechanism of tray arm assembly 100. More specifically, FIG. 4 illustrates a bottom view of tray arm assembly 100, where tray 112 is in an operational state. In an operational state, the tray surface, where consumables and other items may be placed, is horizontal with respect to the ground. FIG. 5, on the other hand, illustrates a top view of tray arm assembly 100, where tray 112 is in a storage state. As shown, as compared to FIG. 4, tray 112 has rotated about the X1 axis, such that the tray surface is vertical with respect to the ground. Placing tray 112 in a storage state allows tray arm assembly 100 and the console to be more conveniently stored, as one of ordinary skill in the art can appreciate.

FIGS. 6A-6B illustrate the two-tier friction mechanism of elbow joint 108 and its corresponding components. In certain embodiments, shoulder joint 104 and/or tray joint 218 include similar components and function similarly. As such, the components and functionality of such a shoulder joint 104 and/or tray joint 218 are not shown or described in detail. However, one of ordinary skill in the art can appreciate how such a shoulder joint 104 and/or tray joint 218 are configured to operate based on the description of the functionality and components of elbow joint 108, described herein.

FIG. 6A illustrates a cross-sectional view of some of the components of elbow joint 108. As shown, elbow joint 108 comprises a cover 652, which covers the inner components of elbow joint 108. Elbow joint 108 also comprises a joint body 626 and a shaft 622, which is configured to rotate within and with respect to joint body 626. Shaft 622 is fixedly coupled to forearm assembly 110. Therefore, rotating forearm assembly 110 causes shaft 622 to rotate in relation to joint body 626. Shaft 622 also comprises a shaft shoulder 623, which refers to a portion of shaft 622 that has a larger outer diameter than the rest of shaft 622. A bearing 624 is positioned between shaft 622 and joint body 626. As shown, bearing 624 includes a flange 625 that is positioned against shaft shoulder 623. Another bearing 638 is also positioned between shaft 622 and a mount assembly 650, which is coupled to joint body 626. Shaft 622 is configured to rotate within bearing 624 and 638.

FIG. 6A also shows a side-view of a pushrod 628 that is configured to slide within shaft 622. As described in more detail in relation to FIG. 6B, pulling release handle 115 causes pushrod 628 to push or actuate elbow lever 646. As shown, pushrod 628 comprises a tail 629 that is positioned to lightly touch elbow lever 646.

As discussed, elbow joint 108 is configured with a two-tier friction mechanism, including the first friction mechanism and the second friction mechanism. The first and the second friction mechanisms work collectively to create static friction between shaft 622 and a number of components of elbow joint 108. However, the first friction mechanism creates a much stronger static friction than the second friction mechanism. When the first friction mechanism is activated, rotating shaft 622 requires overcoming the static friction associated with the first friction mechanism. If a user applies enough torque to shaft 622 to overcome the static friction associated with the first friction mechanism, the static friction associated with the second friction mechanism is also overcome. In such a case the user is able to rotate shaft 622 relative to joint body 626.

When the first friction mechanism is de-activated in elbow joint 108, the second friction mechanism in elbow joint 108 continues to create a drag torque against whipping of the tray arm assembly 100. The second friction mechanism refers to a mechanism or a set of components that operate to press flange 625 of bearing 624 against shaft 622, causing static friction between the two components. When the first friction mechanism is de-activated, in order to rotate shaft 622, the static friction between bearing 624 and shaft 622 has to be overcome. For example, a user may rotate shaft 622 by applying enough torque to shaft 622 (e.g., by attempting to rotate forearm assembly 110) to overcome the static friction between bearing 624 and shaft 622. When enough torque is applied to rotate shaft 622, the static friction creates a light drag torque, which restrains tray arm assembly 100 against a whipping motion.

The set of components that enable the second friction mechanism include a nut 630, a disc spring 632, a thrust bearing 636, bearing 624, and joint body 626. Nut 630 is a fastener with a threaded hole that is configured to be screwed onto an exterior of a segment of shaft 622 that is also threaded. Disc spring 632 is positioned on top of nut 630 and configured to exert pressure on thrust bearing 636. Disc spring 632, in one example, may comprise primarily a convex disc supported at the outer periphery by one force and an opposing force on the center of the disc. In the example of FIG. 6A, disc spring 632's inner periphery is supported by nut 630 and an opposing force is exerted on disc spring 632 by thrust bearing 636. By adjusting the position of nut 630 along shaft 622, the amount of force that disc spring 632 exerts on thrust bearing 636 can be adjusted. For example, screwing nut 630 towards disc spring 632 causes disc spring 632 to exert more force on thrust bearing 636.

The force applied to thrust bearing 636 is transferred to bearing 624 and joint body 626. This force is then transferred by bearing 624 and joint body 626 to shaft shoulder 623, creating static friction between flange 625 of bearing 624 and shaft shoulder 623. When the first friction mechanism is de-activated, this static friction leads to a prevailing drag torque during a rotation of shaft 622.

Moving now to the first friction mechanism, the first friction mechanism refers to a mechanism or a set of components of a slip clutch assembly that operates to create static friction between shaft 622 and joint body 626. The set of components that enable the first friction mechanism include clutch stack 640, disc spring 648, a release ring 642, a pressure plate 644, and a mount assembly 650. Clutch stack 640 comprises a number of friction interfaces including a plurality of first clutch plates that are keyed or coupled to joint body 626, a plurality of second clutch plates that are keyed or coupled to shaft 622, and a plurality of friction discs, each of the plurality of friction discs is positioned between one of the plurality of first clutch plates and one of the plurality of second clutch plates. In certain aspects, the first plurality of clutch plates and the second plurality of clutch plates may include one or more of stainless steel, cast iron, plain steel, etc. In certain aspects, the friction discs may include material such as Kevlar paper. The first friction mechanism is described in more detail with reference to FIG. 6B. Note that activating and deactivating the first friction mechanism may interchangeably be referred to as activating and deactivating the slip clutch assembly.

FIG. 6B illustrates a side view of some of the components of elbow joint 108. More specifically, side views of shaft 622, disc spring 648, release ring 642, pressure plate 644, clutch stack 640 are shown. FIG. 6B also shows a cross-sectional view of joint body 626 and mount assembly 650. Static friction is created between the friction interfaces of clutch stack 640 as a result of force exerted by disc spring 648 on clutch stack 640 through release ring 642 and pressure plate 644. Disc spring 648 functions similar to disc spring 632. However, disc spring 648 is configured to exert roughly constant force on release ring 642, which is in contact with pressure plate 644. Accordingly, release ring 642 transfers the force exerted by disc spring 648 to pressure plate 644, which in turn transfers the force to clutch stack 640. The force applied to clutch stack 640 causes the friction interfaces of clutch stack 640 to be compressed together. Such a compression creates static friction between the friction interfaces. When the first friction mechanism is activated, in order to rotate shaft 622, enough torque needs to be applied to shaft 622 to overcome the static friction in clutch stack 640.

The first friction mechanism in elbow joint 108 is activated unless a user pulls release handle 115 of tray arm assembly 100, which then de-activates the first friction mechanism in elbow joint 108. The user may reactivate the first friction mechanism in elbow joint 108 by releasing release handle 115. FIG. 6B shows a number of components within elbow joint 108 that work to allow the first friction mechanism to be deactivated and reactivated. Such components include elbow lever 646, release link 647, release lever 653, and pin 643 of release ring 642. Release ring 642 is a hollow cylindrical component with two pins positioned around it. As FIG. 6B shows a side view of release ring 642, only one pin 643 is visible. Pin 643 is positioned within a U-shaped portion of release lever 653. Release lever 653 comprises two flanges 657 and 655. As shown, one end of release link 647 is positioned within flange 655. Also, a pin is inserted through the openings of flange 655 as well as the opening of the end of release link 647. The other end of release link 647 is coupled (e.g., indirectly) to elbow lever 646. Also, a pin is inserted through the openings of flange 657 as well as two holes in joint body 626.

When a user pulls release handle 115, pushrod 628 pushes elbow lever 646 away from clutch stack 640 causing elbow lever 646 to rotate, which pushes release link 647 and flange 655 causing release lever 653 to rotate and lift release ring 642, separating release ring 642 from pressure plate 644. More specifically, pushing release lever 653 away from pressure plate 644 causes release lever 653 to exert force on pin 643, causing pin 643 to be pushed away from pressure plate 644. When release ring 642 is pushed away from pressure plate 644, release ring 642 and pressure plate 644 are separated, such that release ring 642 and pressure plate 644 are no longer in contact. In such a state, the force or compressive load exerted by disc spring 648 on release ring 642 is not transferred to pressure plate 644, meaning that clutch stack 640 is no longer compressed. When clutch stack 640 is not compressed, the static friction between the friction interfaces of clutch stack 640 is removed, eliminated, or at least reduced significantly and, thereby, the first friction mechanism is de-activated. Note that, in certain aspects, the length of pushrod 628 within shaft 622 is adjustable to allow for the removal of any slack in the linkage between release handle 115 and release ring 642. Also, note that although in the embodiments described herein disc springs 648 and 632 are used, in some other embodiments, other types of springs may be used.

Figure 6C:
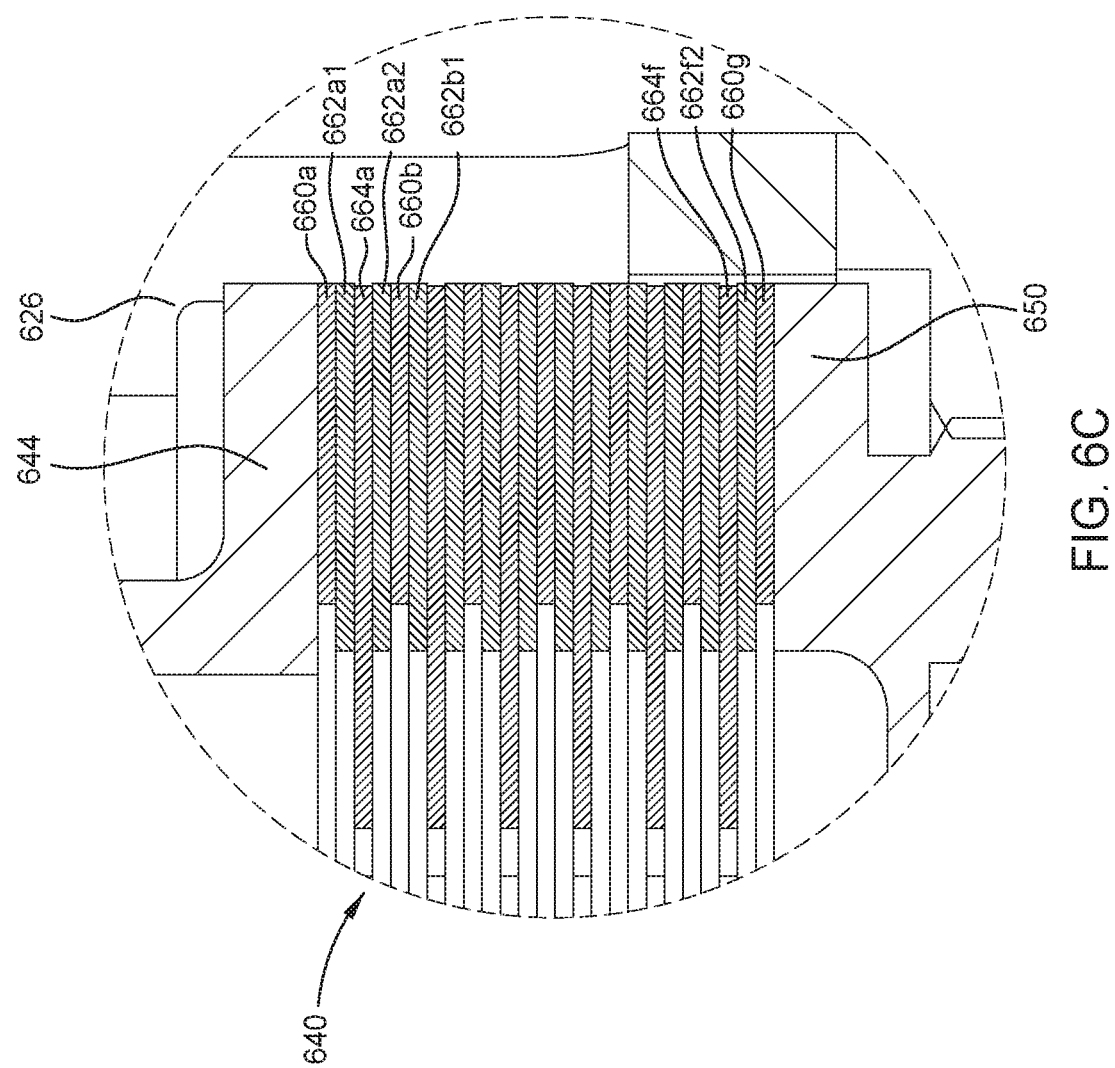
FIG. 6C illustrates example friction interfaces of a clutch stack of the elbow joint of FIGS. 6A-6B in more detail, in accordance with certain embodiments of the present disclosure.

FIG. 6C illustrates the friction interfaces of clutch stack 640 in more detail. As shown, clutch stack 640 is compressed between pressure plate 644 and mount assembly 650. The friction interfaces of clutch stack 640 comprise a plurality of first clutch plates 660 that are keyed or coupled to joint body 626, a plurality of second clutch plates 664 that are keyed or coupled to shaft 622 (not shown in FIG. 6C), and a plurality of friction discs 662, where each of the plurality of friction discs 662 is positioned between one of the plurality of first clutch plates 660 and one of the plurality of second clutch plates 664. For example, friction disc 662a1 is positioned between clutch plate 660a and clutch plate 664a while friction disc 662a2 is positioned between clutch plate 660b and clutch plate 664a. Similarly, friction disc 662f2 is positioned between clutch plate 664f and clutch plate 660g, and so on. Although in the example of FIG. 6C, clutch plates 660 are positioned at the two ends of clutch stack 640, in some other examples, clutch plates 664 are instead positioned at the two ends of clutch stack 640. Also, in different embodiments, there may be a larger or smaller number of friction interfaces in clutch stack 640.

Figure 7:
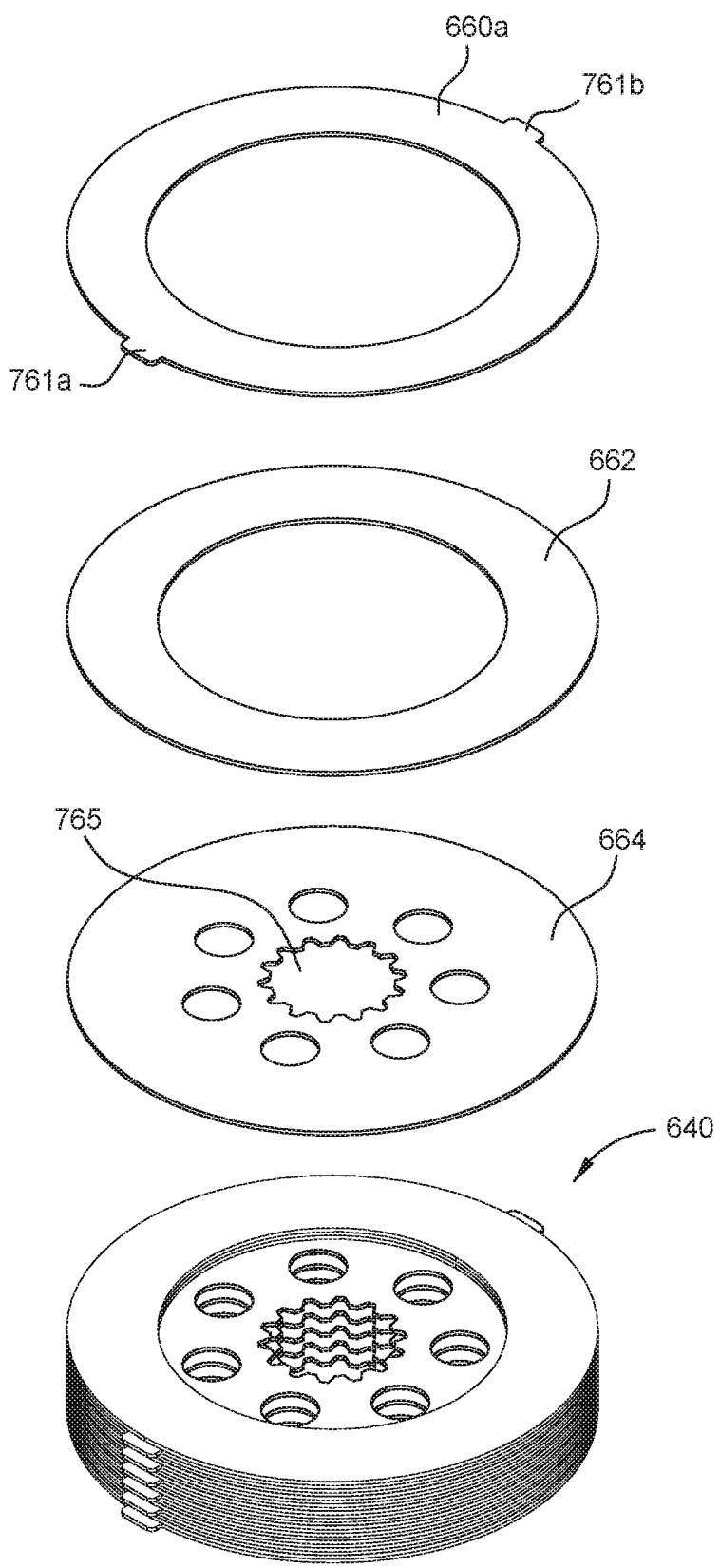
FIG. 7 illustrates an example clutch plate, friction disc, and clutch plate of the clutch stack of FIG. 6C, in accordance with certain embodiments of the present disclosure.
Figure 8:
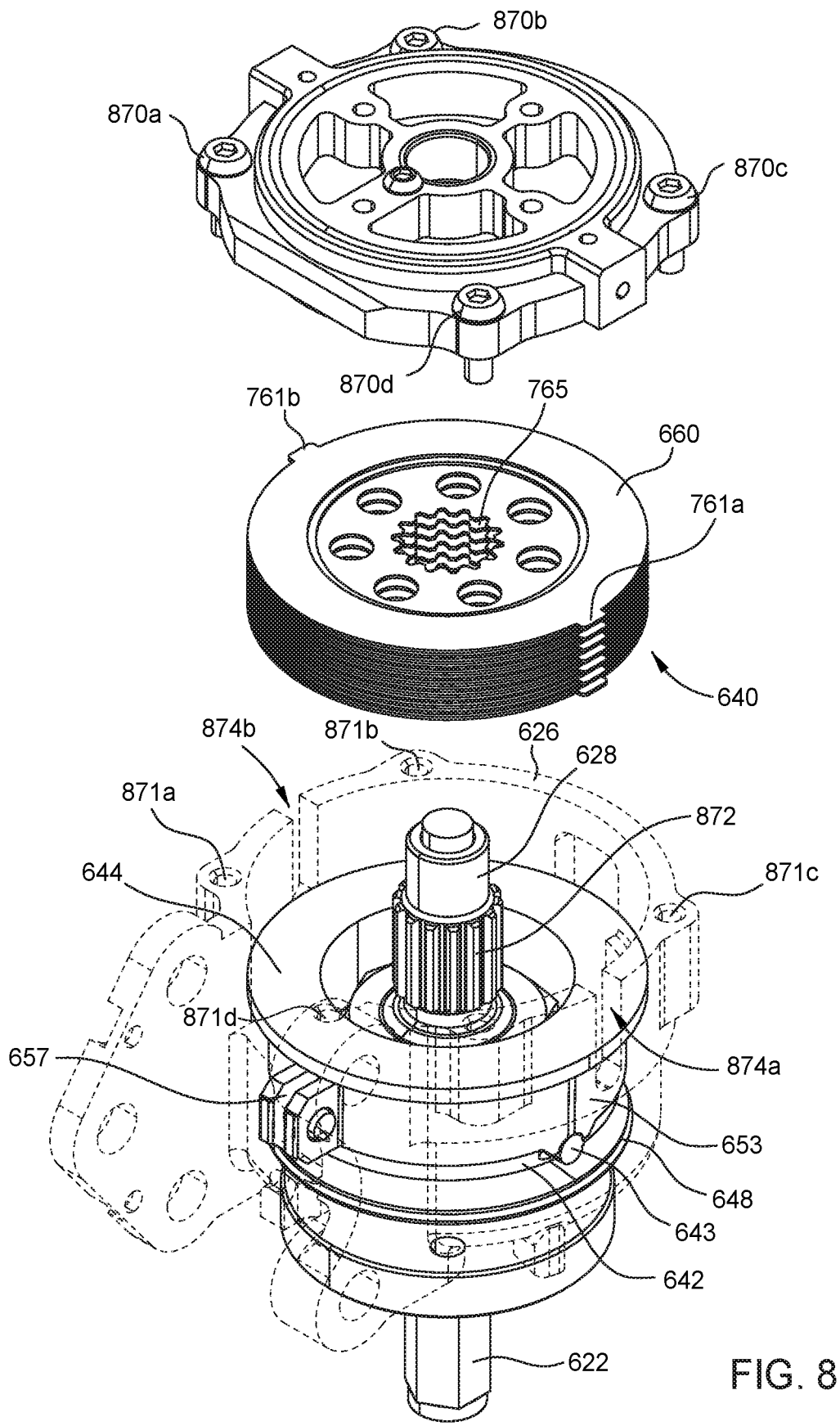
FIG. 8 illustrates an exploded view of the elbow joint of FIGS. 6A-6B and some of its components, in accordance with certain embodiments of the present disclosure.

FIG. 7 illustrates a clutch plate 660a, a friction disc 662, and a clutch plate 664. As shown, clutch plate 660 comprises key features (e.g., tabs) 761a and 761b that are configured to slide into keyed elements (e.g., openings) on the sides of a joint body, as shown in FIG. 8. Note that although in the example of FIG. 7 clutch plate 660 has two key features, in certain embodiments, clutch plate 660 may include any number of key features (e.g., more than two). Also, the joint body may include one or more keyed elements, such as one or more openings. Clutch plate 664 also comprises a key feature 765, which in the example of FIG. 7 is a keyed opening that allows clutch plate 664 to be coupled to or engaged by a key element (e.g., spline-shaped segment of shaft 622, as shown in FIG. 8) of shaft 622. FIG. 7 also provides a top view of an assembled clutch stack 640, which comprises a plurality of clutch plates 660, a plurality of clutch plates 664, and a plurality of friction discs 662. As discussed, a key element of shaft 622 is configured to pass through clutch stack 640 and engage key features 765 of clutch plates 664. Note that the purpose of key features 761a-b is to key clutch plates 660 to a joint body (e.g., joint body 626) and the purpose of key features 756 is to key clutch plates 664 to a shaft (e.g., shaft 622). However, in some other embodiments, other techniques or key features, and/or elements may be used to achieve these purposes. For example, instead of keyed openings 756 that is configured to be keyed to a spline-shaped segment (shown in FIG. 8), in some aspects, keyed openings 756 may instead be configured to be keyed to a keyed element of shaft 622 that has a different shape.

FIG. 8 illustrates an exploded view of elbow joint 108 and some of its components. For example, FIG. 8 illustrates mount assembly 650, which is mounted to joint body 626 using screws 870a-870d. As shown, screws 870a-870d are configured to be screwed to screw holes 871a-871d. FIG. 8 also illustrates clutch stack 640 comprising a plurality of friction interfaces, including a plurality of clutch plates 660, each having key features 761a and 761b. As discussed, key element 872 of shaft 622 is inserted through key features 765 of clutch plates 664 such that by rotating shaft 622, key element 872 engages clutch plates 664 and rotates clutch stack 640. In the example of FIG. 8, key element 872 refers to a spline-shaped segment of shaft 622. When assembling elbow joint 108, clutch stack 640 passes through key element 872 while key features 761a and 761b slide in key elements 874a and 874b, respectively, of joint body 626. In the example of FIG. 8, key elements 874a-b are openings in joint body 626. Positioning key features 761a and 761b within openings 874a and 874b of joint body 626 ensure that clutch plates 660 are keyed to joint body 626. In some other embodiments, other types of key elements may be used in the joint body 626 to ensure that clutch plates 660 are keyed to joint body 626.

Once clutch stack 640 is inserted through the key element 872 of shaft 622, it makes contact with pressure plate 644, which itself makes contact with release ring 642 having pin 643. Release lever 653, having flanges 657 and 655, is also positioned such as to push pin 643 away from clutch stack 640 when an elbow lever (e.g., elbow lever 646) is actuated as a result of a pushrod pressing on the elbow lever.

Figure 9:
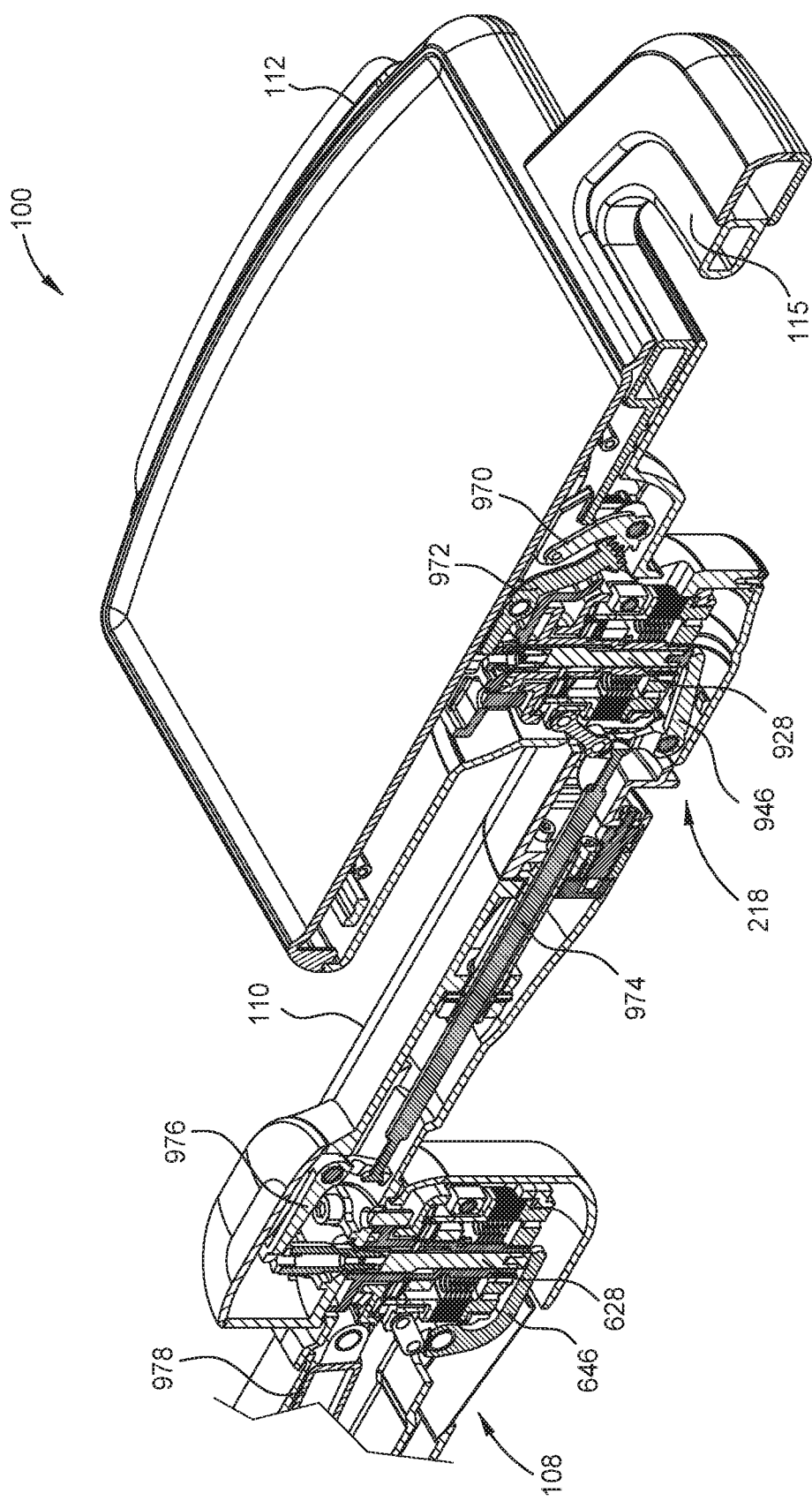
FIG. 9 illustrates a portion of the tray arm assembly of FIG. 1, in accordance with certain embodiments of the present disclosure.
Figure 10:
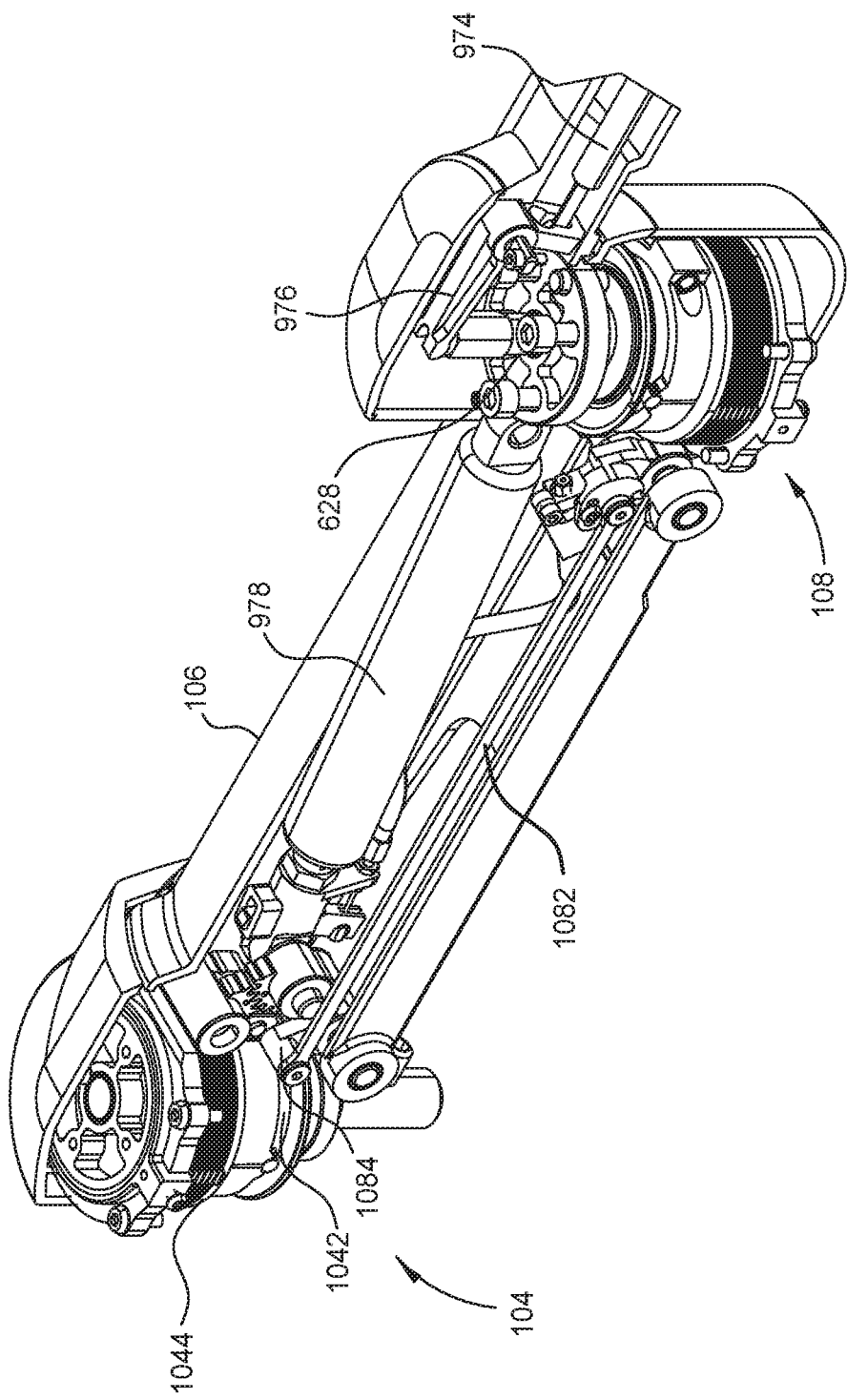
FIG. 10 illustrates another portion of the tray arm assembly of FIG. 1, in accordance with certain embodiments of the present disclosure.

Although FIGS. 6A-8 illustrate elbow joint 108 and its components, as discussed, shoulder joint 104 and/or tray joint 218 may include the same two-tier friction mechanism, although certain elements and components, relating to how the first friction mechanism in each of those joints is de-activated, may be different from joint to joint. FIGS. 9 and 10 illustrate how pulling release handle 115 of tray arm assembly 100, in an embodiment, causes the first friction mechanism in each joint to be de-activated, in which case the second friction mechanism in each joint still works to create a drag torque to prevent the whipping of tray arm assembly 100.

FIG. 9 illustrates a portion of tray arm assembly 100, including tray 112, which is coupled to tray joint 218 that is positioned at one end of forearm assembly 110. As shown, the other end of forearm assembly 110 is coupled to elbow joint 108. By pulling release handle 115, the user can actuate gear elements 970 and 972, which are configured to cause pushrod 928 (e.g., similar to pushrod 628) to be pressed against wrist lever 946. Pressing wrist lever 946 away from tray 112 de-activates the first friction mechanism in tray joint 218 while at the same time pulling forearm link 974. Pulling forearm link 974 actuates lever 976, which presses pushrod 628 towards elbow lever 646 and, therefore, actuates elbow lever 646. When actuated, elbow lever 646 de-activates the first friction mechanism in elbow joint 108, actuates a release pin in gas spring 978, and also pulls an upper arm link (shown in FIG. 10) towards elbow joint 108.

FIG. 10 illustrates another portion of tray arm assembly 100, including elbow joint 108 at one end of upper arm assembly 106 and shoulder joint 104 at the other end. As discussed, when actuated, the elbow lever (not shown in FIG. 10) de-activates the first friction mechanism in elbow joint 108, actuates a release pin in gas spring 978, and also pulls upper arm link 1082 towards elbow joint 108. An example of how gas spring 978 may function, in certain aspects, is described in U.S. Pat. No. 7,461,825. When the pin in gas spring 978 is released, the user is able to elevate or lower tray arm assembly 100, as shown in FIGS. 2-3. Pulling upper arm link 1082 towards elbow joint 108 actuates a series of gears 1084, which then causes a separation of the release ring 1042 and the pressure plate 1044 of shoulder joint 104 and, thereby, a de-activation of the first friction mechanism in shoulder joint 104. Accordingly, pulling release handle 115 causes the first friction mechanism in each of the joints to be de-activated. In such a state, a user is able to easily move the location of the tray in relation to the console. However, as described above, each of the joints is still subject to the second friction mechanism, which prevents the whipping of tray arm assembly 100 relative to the console.

Figure 11:
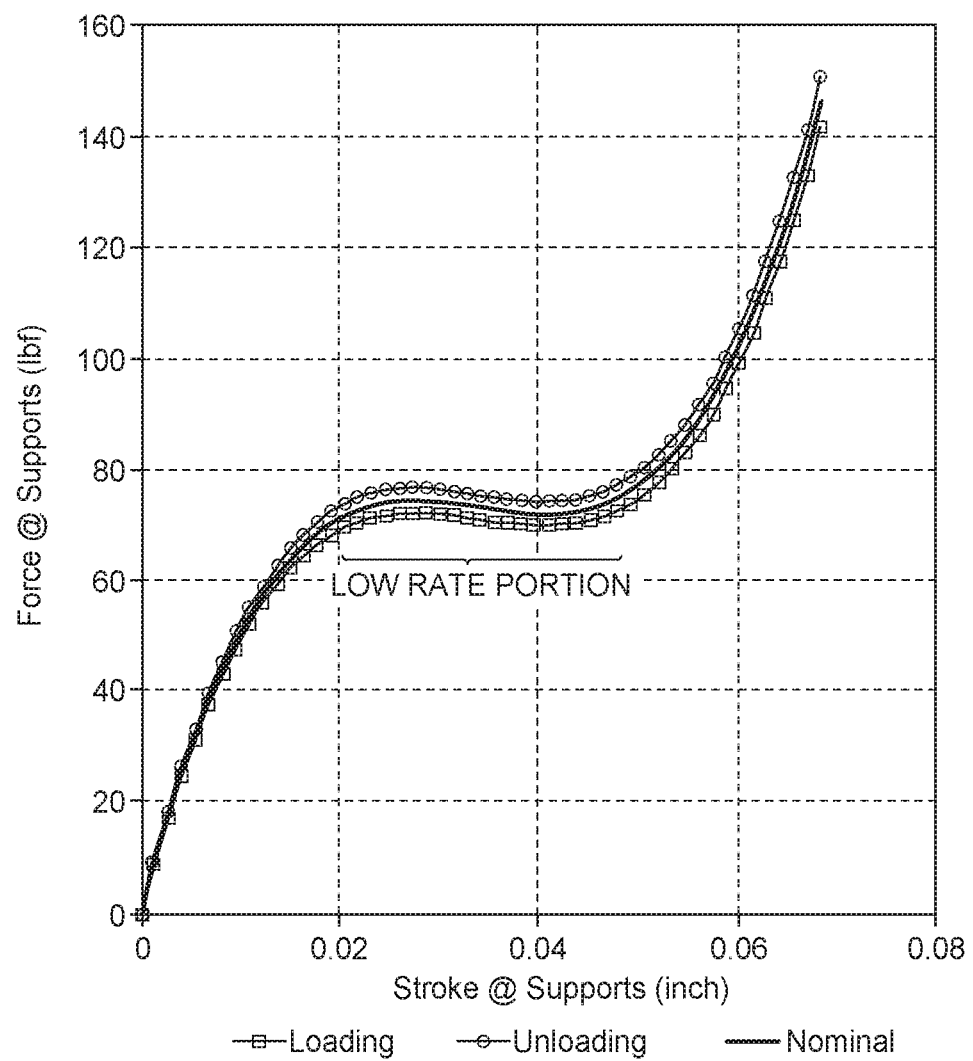
FIG. 11 illustrates force-deflection characteristics of a disc spring designed to operate in a flattened state, in accordance with certain embodiments of the present disclosure.

FIG. 11 illustrates a curve corresponding to the force-deflection characteristics of a disc spring (e.g., disc spring 648, disc spring 632, etc.) designed to operate in a flattened state. A flattened state of a disc spring refers to a state where a normally cone-shaped disc spring is flat or close to being flat because of compression. When a disc spring operates in the flattened state, relatively small changes in force result from relatively large changes in deflection. In other words, in the flattened state, the disc spring operates in a low rate portion of its force-deflection curve. The low rate portion of the force-deflection curve refers to a portion of the curve where, on average, the rate of change in force over the rate of change in deflection (e.g., the slope of the curve) is low. An example of this low rate portion is shown in FIG. 11.

In such a state, a roughly constant force generated by the disc spring translates to a nearly constant force required by the user when actuating release handle 115. Additionally, setting the disc spring to operate in the flattened state allows for wear compensation in both the clutch stack 640 components or any two joint components configured to interface with each other. In certain embodiments, both disc spring 648 and 632 are configured to operate in a low rate portion of their force-deflection curve.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A joint of a tray arm assembly, comprising:
   a joint body;
   a shaft configured to rotate relative to the joint body about a longitudinal axis of the shaft;
   a slip clutch assembly, comprising:
      a clutch stack, comprising:
         a plurality of first clutch plates keyed to the shaft; and
         a plurality of second clutch plates keyed to the joint body;
      a spring configured to selectively exert a force on the clutch stack, wherein:
         the force compresses the clutch stack causing a friction between the plurality of first clutch plates and the plurality of second clutch plates with respect to a rotation of the shaft relative to the joint body; and
   a pushrod positioned centrally within the shaft to actuate the clutch stack in response to actuation of the pushrod.

2. The joint of claim 1, wherein:
   the joint is part of a tray arm assembly, and
   the shaft is fixedly coupled to an arm of the tray arm assembly.

3. The joint of claim 1, further comprising:
   a release ring; and
   a pressure plate, wherein:
      the spring is configured to selectively exert the force on the release ring;
      the release ring is configured to transfer the force to the pressure plate; and
      the pressure plate is configured to transfer the force to the clutch stack.

4. The joint of claim 3, further comprising a release lever, wherein:
   actuating the release lever deactivates the slip clutch assembly by separating the release ring from the pressure plate;
   separating the release ring from the pressure plate uncompresses the clutch stack; and
   the friction is reduced when the clutch stack is uncompressed.

5. The joint of claim 4, wherein the release lever is actuated due to force exerted on the release lever by the pushrod.

6. The joint of claim 1, wherein:
   the plurality of first clutch plates comprise first key features; and the first key features are configured to be keyed to corresponding one or more first key elements of the joint body to key the plurality of first clutch plates to the joint body.

7. The joint of claim 6, wherein each of the first clutch plates comprises one or more first key features.

8. The joint of claim 6, wherein:
the first key features comprise tabs;
the one or more first key elements comprise one or more openings; and
the first key features being configured to be keyed to the corresponding one or more first key elements comprise the tabs being configured to slide through the one or more openings.

9. The joint of claim 6, wherein:
the plurality of second clutch plates comprise second key features;
the shaft comprises a second key element that is configured to be inserted into the second key features and engage the plurality of second clutch plates; and
rotating the shaft causes rotation of the plurality of second clutch plates in relation to the plurality of first clutch plates.

10. The joint of claim 9, wherein:
the second key features comprise keyed openings; and
the second key element comprises a spline-shaped segment.

11. The joint of claim 1, wherein:
the clutch stack further comprises a plurality of friction discs;
each of the plurality of friction discs is positioned between one of the plurality of first clutch plates and one of the plurality of second clutch plates; and
the force compresses the clutch stack causing the friction between the plurality of first clutch plates, the plurality of friction discs, and the plurality of second clutch plates with respect to the rotation of the shaft relative to the joint body.

12. The joint of claim 1, wherein the spring comprises a disc spring configured to operate in a low rate portion of its force-deflection curve.

13. A joint of a tray arm assembly, comprising:
a joint body;
a shaft configured to rotate relative to the joint body about a longitudinal axis of the shaft;
a slip clutch assembly, comprising:
a clutch stack, comprising:
a plurality of first clutch plates keyed to the shaft; and
a plurality of second clutch plates keyed to the joint body; and
a spring configured to selectively exert a force on the clutch stack, wherein:
the force compresses the clutch stack causing a friction between the plurality of first clutch plates and the plurality of second clutch plates with respect to a rotation of the shaft relative to the joint body;
a bearing positioned between the joint body and the shaft;
a nut screwed on to an outer segment of the shaft;
a second spring pressed by the nut against a thrust bearing;
the thrust bearing positioned between the second spring and bearing;
the second spring exerts force on the thrust bearing;
the thrust bearing transfers the force to the bearing; and
the force exerted on the bearing creates a second friction between the bearing and the shaft.

14. The joint of claim 13, wherein:
the second spring comprises a disc spring; and
the disc spring is configured to operate in a low rate portion of its force-deflection curve.

15. The joint of claim 13, wherein upon deactivation of the slip clutch assembly the second friction creates a drag torque during the rotation of the shaft.

* * * * *